(12) United States Patent
Mokelke et al.

(10) Patent No.: US 9,795,778 B2
(45) Date of Patent: Oct. 24, 2017

(54) MULTI-ELECTRODE LEAD WITH BACKING FOR MECHO/BARORECEPTOR STIMULATION

(71) Applicant: Cardiac Pacemakers, Inc., St. Paul, MN (US)

(72) Inventors: Eric A. Mokelke, White Bear Lake, MN (US); Shantha Arcot-Krishnamurthy, Vadnais Heights, MN (US); Brian Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 317 days.

(21) Appl. No.: 14/327,284

(22) Filed: Jul. 9, 2014

(65) Prior Publication Data

US 2015/0018918 A1    Jan. 15, 2015

Related U.S. Application Data

(60) Provisional application No. 61/846,045, filed on Jul. 14, 2013.

(51) Int. Cl.
 *A61N 1/05* (2006.01)
 *A61N 1/36* (2006.01)

(52) U.S. Cl.
 CPC .............. *A61N 1/05* (2013.01); *A61N 1/0553* (2013.01); *A61N 1/36117* (2013.01)

(58) Field of Classification Search
 CPC .................................... A61N 1/05; A61N 1/36
 USPC ........................................... 607/116–117, 46
 See application file for complete search history.

(56) References Cited

U.S. PATENT DOCUMENTS

| | | | |
|---|---|---|---|
| 5,476,493 A * | 12/1995 | Muff | A61N 1/057 604/175 |
| 5,674,272 A | 10/1997 | Bush et al. | |
| 6,564,079 B1 | 5/2003 | Cory et al. | |
| 6,909,920 B2 | 6/2005 | Lokhoff et al. | |
| 6,985,774 B2 | 1/2006 | Kieval et al. | |
| 7,006,875 B1 * | 2/2006 | Kuzma | A61N 1/0556 600/372 |
| 7,015,061 B2 | 3/2006 | Lu et al. | |
| 7,337,005 B2 | 2/2008 | Kim et al. | |

(Continued)

FOREIGN PATENT DOCUMENTS

CN    101244315 A    8/2008
EP    1487535 B1    12/2004

(Continued)

OTHER PUBLICATIONS

International Search Report and Written Opinion issued in PCT/US2014/046008, dated Oct. 1, 2014, 12 pages.

(Continued)

*Primary Examiner* — Christopher D Koharski
*Assistant Examiner* — Roland Dinga
(74) *Attorney, Agent, or Firm* — Faegre Baker Daniels LLP (57) ABSTRACT

An electrode structure for an implantable stimulation lead for use in stimulating a target nerve structure within a patient includes a flexible backing defined by a major dimension extending in a direction of a first axis, and a minor dimension extending generally orthogonal to the first axis. The electrode structure also includes a plurality of electrodes coupled to the backing.

17 Claims, 8 Drawing Sheets

(56) References Cited

U.S. PATENT DOCUMENTS

| | | |
|---|---|---|
| 7,445,953 B2 | 11/2008 | Lu et al. |
| 7,502,650 B2 | 3/2009 | Kieval |
| 7,616,997 B2 | 11/2009 | Kieval et al. |
| 7,813,812 B2 | 10/2010 | Kieval et al. |
| 8,126,560 B2 | 2/2012 | Scheiner et al. |
| 8,175,705 B2 | 5/2012 | Libbus |
| 8,571,664 B2 | 10/2013 | Anderson et al. |
| 8,901,268 B2 | 12/2014 | Krishnamoorthy et al. |
| 8,948,872 B2 | 2/2015 | Shuros et al. |
| 2002/0095080 A1 | 7/2002 | Cory et al. |
| 2003/0187490 A1 | 10/2003 | Gliner |
| 2004/0176759 A1 | 9/2004 | Krishnamurthy et al. |
| 2005/0085884 A1 | 4/2005 | O'Brien et al. |
| 2005/0096710 A1 | 5/2005 | Kieval |
| 2005/0182456 A1 | 8/2005 | Ziobro et al. |
| 2006/0085049 A1 | 4/2006 | Cory et al. |
| 2006/0276704 A1 | 12/2006 | McGinnis et al. |
| 2007/0021792 A1 | 1/2007 | Kieval et al. |
| 2007/0027512 A1 | 2/2007 | Chan et al. |
| 2007/0208391 A1 | 9/2007 | Wahlstrand et al. |
| 2008/0004673 A1 | 1/2008 | Rossing et al. |
| 2008/0046051 A1 | 2/2008 | Skubitz et al. |
| 2008/0147146 A1 | 6/2008 | Wahlgren et al. |
| 2009/0132002 A1 | 5/2009 | Kieval |
| 2009/0143837 A1 | 6/2009 | Rossing et al. |
| 2009/0234418 A1 | 9/2009 | Kieval et al. |
| 2010/0152826 A1* | 6/2010 | Tanabe ............... A61N 1/0587 607/129 |
| 2010/0324641 A1 | 12/2010 | Skubitz et al. |
| 2011/0257716 A1 | 10/2011 | Tiedtke |
| 2013/0018247 A1 | 1/2013 | Glenn et al. |
| 2015/0165215 A1 | 6/2015 | Mokelke et al. |
| 2015/0231391 A1 | 8/2015 | Mokelke |
| 2015/0366465 A1 | 12/2015 | De Kock et al. |
| 2015/0366467 A1 | 12/2015 | De Kock et al. |

FOREIGN PATENT DOCUMENTS

| | | |
|---|---|---|
| EP | 2108398 B1 | 10/2009 |
| EP | 1487535 B1 | 6/2012 |
| JP | 2004526471 A | 9/2004 |
| JP | 2009532102 A2 | 9/2009 |
| JP | 2009532185 A | 9/2009 |
| JP | 2012130579 A | 7/2012 |
| KR | 20120053090 A | 5/2012 |
| WO | 0226314 A1 | 4/2002 |
| WO | 2007118090 A2 | 10/2007 |
| WO | 2015195980 A1 | 12/2015 |
| WO | 2015195982 A2 | 12/2015 |

OTHER PUBLICATIONS

International Search Report arid Written Opinion issued in PCT/US2015/036526, dated Oct. 26, 2015, 12 pages.
International Search Report and Written Opinion Issued in PCT/US2015/036528, dated Jan. 19, 2016, 15 pages.
Invitation to Pay Additional Fees and, Where Applicable, Protest Fee issued in PCT/US2015/036528, dated Oct. 28, 2015, 6 pages.
International Preliminary Report on Patentability issued in PCT/US2014/046008, dated Jan. 28, 2016, 8 pages.
International Search Report and Written Opinion issued in PCT/US2015/050303, dated Jan. 14, 2016, 12 pages.
International Preliminary Report on Patentability issued in PCT/US2015/036526, dated Dec. 20, 2016, 8 pages.
International Preliminary Report on Patentability issued in PCT/US2015/036528, dated Dec. 20, 2016, 9 pages.
International Preliminary Report on Patentability issued in PCT/US2015050303, dated Mar. 30, 2017, 8 pages.

* cited by examiner

MULTI-ELECTRODE LEAD WITH BACKING FOR MECHO/BARORECEPTOR STIMULATION

CROSS-REFERENCE TO RELATED APPLICATION

This application claims priority to U.S. Provisional Application 61/846,045, filed Jul. 14, 2013, which is herein incorporated by reference in its entirety.

TECHNICAL FIELD

The disclosure relates to systems and methods for stimulating nerves. More particularly, the disclosure relates to systems and corresponding methods for stimulating the baroreceptors of the carotid sinus.

BACKGROUND

The use of nerve stimulation for treating and controlling a variety of medical, psychiatric, and neurological disorders has seen significant growth over the last several decades, including for treatment of heart conditions (e.g., hypertension), epilepsy, obesity, and breathing disorders, among others.

SUMMARY

Disclosed herein are various embodiments of electrode structures for neurostimulation leads.

In Example 1, an electrode structure for an implantable stimulation lead for use in stimulating a target nerve structure within a patient includes a flexible backing defined by a major dimension extending in a direction of a first axis, and a minor dimension extending generally orthogonal to the first axis. The electrode also includes a plurality of electrodes coupled to the backing.

In Example 2, the electrode structure according to Example 1, wherein the backing is adapted to be coupled to a distal end of an implantable lead in situ.

In Example 3, the electrode structure according to Example 1 or 2, wherein the backing is configured to resist suture tearing.

In Example 4, the electrode structure according to any of Examples 1-3, wherein at least a portion of the backing element includes an embedded mesh.

In Example 5, the electrode structure according to any of Examples 1-4, wherein at least a portion of a first surface of the backing element comprises one or more grooves adapted to hold at least a portion of a suture.

In Example 6, the electrode structure according to any of Examples 1-5, wherein the backing has a curved shape adapted to conform to a curvature of a blood vessel.

In Example 7, a neurostimulation lead includes a lead body having a proximal portion and a distal portion, a first conductor extending through the lead body and an electrode structure secured to the distal portion of the lead body. The electrode structure includes a backing defined by a major dimension generally in a direction of a longitudinal axis defined by the distal portion of the lead body and a minor dimension generally in a same plane and orthogonal to the longitudinal axis and a plurality of electrodes coupled to at least a portion of the backing.

In Example 8, the neurostimulation lead according to Example 7, wherein the backing is generally rectangular in shape.

In Example 9, the neurostimulation lead according to Example 7 or 8, wherein the backing has peripheral edges that are generally rounded.

In Example 10, the neurostimulation lead according to any of Examples 7-9, wherein the backing is generally oval-shaped.

In Example 11, the neurostimulation lead according to any of Examples 7-10, wherein the backing is curved about a central axis generally parallel to a longitudinal axis.

In Example 12, a neurostimulation system includes a pulse generator comprising a power source and a lead that includes a lead body having a proximal portion and a distal portion, the proximal portion of the lead secured to the pulse generator. The lead also includes a first conductor extending through the lead body and an electrode structure secured to the distal portion of the lead body. The electrode structure includes a backing defined by a major dimension generally in a direction of a longitudinal axis defined by the distal portion of the lead and a minor dimension generally in a same plane and orthogonal to the longitudinal axis, and a plurality of electrodes coupled to at least a portion of the backing.

In Example 13, the neurostimulation system according to Example 12, wherein the backing includes a flexible material that includes a mesh.

In Example 14, the neurostimulation system according to Example 12 or 13, wherein the mesh is disposed in an area proximate to an outer perimeter.

In Example 15, the neurostimulation system according to any of Examples 12-14, wherein the mesh is disposed uniformly over an entire portion of the backing.

In Example 16, the neurostimulation system according to any of Examples 12-15, wherein the mesh comprises polyester.

In Example 17, the neurostimulation system according to any of Examples 12-16, wherein the backing includes grooves or holes adapted to guide suture placement.

In Example 18, the neurostimulation system according to any of Examples 12-17, wherein the grooves or holes extend across at least a portion of the backing.

In Example 19, the neurostimulation system according to any of Examples 12-18, wherein the grooves or holes extend across one of a proximal portion, a distal portion of the backing or a combination thereof.

In Example 20, the neurostimulation system according to any of Examples 12-19, wherein the major dimension of the backing ranges from about 12 mm to about 16 mm.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
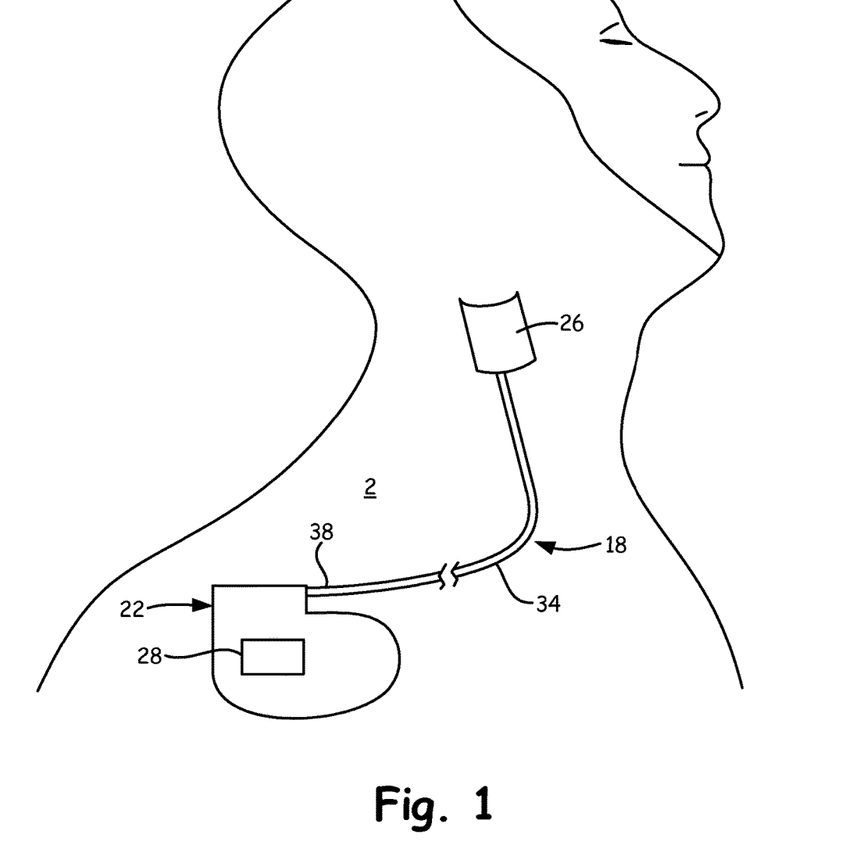
FIG. 1 is a schematic view of a neurostimulation system according to some embodiments.

FIG. 1 is a schematic illustration showing a system 2 for stimulating a region of a patient's nervous system. In one embodiment, the system 2 can be particularly effective in stimulating the baroreceptors of the carotid sinus for treatment of heart conditions such as hypertension.

As shown, the system 2 includes a neurostimulation lead 18 and an implantable pulse generator 22. As further shown, the neurostimulation lead 18 includes an electrode structure 26 and a lead body 34. In various embodiments, and as explained in greater detail herein, the neurostimulation lead 18 and the electrode structure 26 cooperate to form a stimulation electrode assembly. In the illustrated embodiment, the neurostimulation lead 18 is coupled to the pulse generator 22, which includes a power source or battery 28. Additionally, the electrode structure 26 is disposed at an implantation location within the patient. In one embodiment, the implantation location is a location on or adjacent to the carotid sinus for selective stimulation of the carotid sinus baroreceptors.

As will be further explained herein, in various embodiments, the neurostimulation lead 18 and the electrode structure 26 can be provided as separate elements that are coupled together in situ during the implantation process. Alternatively, in various embodiments, the neurostimulation lead 18 and the electrode structure 26 can be a unitary element, with the neurostimulation lead 18 housing electrical conductors that are electrically connected to electrodes on the electrode structure 26.

In various embodiments, the lead body 34 is elongate and flexible and is made of a biocompatible electrically insulative material, and includes a proximal end 38 coupled to the pulse generator 22 via a connector (not shown). In various embodiments, the lead body 34 is generally flexible to allow for patient movement. In some embodiments, the lead body 34 can include one or more guide lumens to receive a guide member such as a guidewire or stylet in order to stiffen the lead body 34 for surgical implantation.

According to various embodiments, the neurostimulation lead 18 can include a plurality of conductors (not shown) including individual wires, coils, or cables extending within the lead body 34 from the proximal end 38 in a direction to the electrode structure 26. The conductors can be insulated with an insulator such as silicone, polyurethane, ethylene tetrafluoroethylene, or another biocompatible, insulative polymer. In one exemplary embodiment, the conductors have a co-radial design. In some embodiments, each individual conductor is separately insulated and then wound together in parallel to form a single coil. In another exemplary embodiment, the conductors have a co-axial, non-co-radial configuration. In various embodiments, the individual conductors may be single or multi-filar coil conductors. In still other embodiments, one or more of the conductors is a stranded cable conductor each routed through one of the aforementioned lumens in the lead body 34. In short, the various embodiments are not limited to any particular conductor configuration within the neurostimulation lead 18.

In various embodiments, the electrode structure 26 can have a number of suitable configurations that are able to effectively stimulate the target nerves such as the carotid sinus baroreceptors. In the embodiment illustrated in FIG. 1, after being implanted in the patient and assembled, the electrode structure 26 has a generally curved shape that can surround or encircle a portion or the entire implantation site. In the illustrated embodiment, the electrode structure 26 may be configured to be wrapped fully around the implantation site, but in alternative embodiments the electrode structure 26 can be configured to wrap around only a portion of the circumference of the implantation site.

Figure 2A:
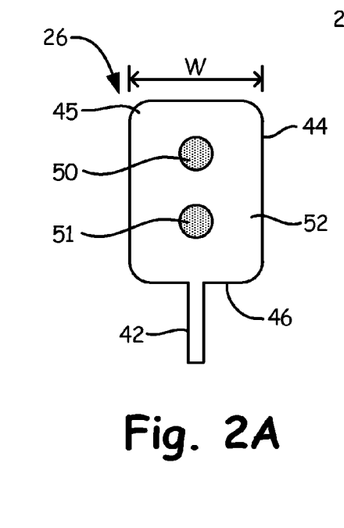
FIGS. 2A-C are schematic front, side and rear views, respectively, of a portion of a neurostimulation lead for the neurostimulation system of FIG. 1, according to some embodiments.
Figures 2B, 2C:
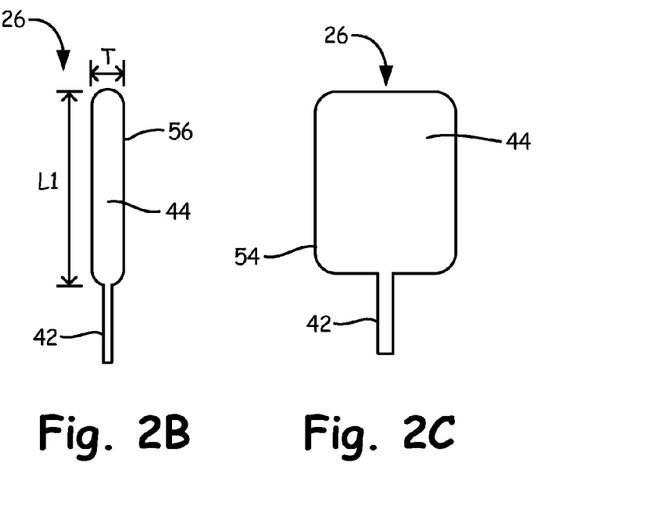

FIGS. 2A-C are schematic front, side and rear views, respectively, of the electrode structure 26 according to various embodiments. As shown in FIG. 2A, the electrode structure includes a backing 44 and a pair of electrodes 50, 51. In some embodiments, the electrode structure 26 may include more than two electrodes 50, 51. As further shown, in various embodiments, the electrode structure 26 extends from or is integrally coupled to a distal end 42 of the lead body 34 (see FIG. 1).

As shown in FIGS. 2A-C, the backing 44 has a first surface 52, a second opposite surface 54 and sides 56 extending between the first surface 52 and the second surface 54. The electrode structure 26 also has a distal portion 45 and a proximal portion 46.

In various embodiments, the electrodes 50, 51 are disposed onto the first surface 52 of the backing 44 and/or disposed within at least a portion of the backing 44. In various embodiments, the electrodes 50, 51 may be positioned flush against the first surface 52 of the backing 44. In other embodiments, the electrodes 50, 51 may protrude from the first surface 52 of the backing 44. In some embodiments, the electrodes 50, 51 may be recessed from the first surface 52 and into the backing 44.

Each electrode 50, 51 may be of any suitable dimension that is capable of delivering energy to a desired site to stimulate tissue. In some embodiments, the electrodes 50, 51 can be a disc shape that includes a disc-like cap-and-stem form. For example, the head of each of the electrodes 50, 51 may have a circular diameter ranging from between about 0.5 mm to 3 mm. A suitable diameter of the disc-shaped electrodes 50, 51 may be 2 mm, for example. In other embodiments, the electrodes 50, 51 can be helically shaped, a flexible ribbon, or cylindrical shaped. In other embodiments, the electrodes 50, 51 may be spherically shaped (ball) tip mounted to a rod.

In various embodiments, the backing 44 of the electrode structure 26 can be formed from a flexible, electrically insulative material. Suitable polymers that may be used for the backing 44 can include, for example, silicone, polyurethane, polysiloxane urethane, ethylene tetrafluoroethylene (ETFE), polytetrafluoroethylene (PTFE), expanded PTFE (ePTFE), and expanded ultra-high-molecular-weight polyethylene (eUHMWPE), polyisobutylene-based polyurethanes (PIB PU), although others are also contemplated.

Suitable materials for the electrodes 50, 51 include conductive materials such as platinum, titanium, or a platinum-based alloy, for example, platinum-iridium. In some embodiments, the electrodes 50, 51 may also include a coating disposed over the conductive material. Suitable coatings may include, for example, iridium, iridium oxide, platinum gray, titanium nitride, and platinum black.

In some embodiments, at least a portion of the exposed surfaces of the electrodes 50, 51 may include features to increase the surface area of the electrodes 50, 51. Examples of features that increase the surface area include grooves, dimples, texturing or other similar features.

Figures 3A, 3B:
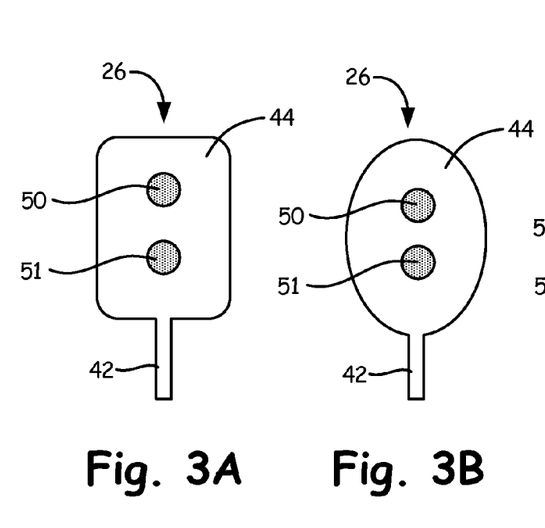
FIGS. 3A-C are schematic views of various embodiments of an electrode structure for the neurostimulation lead of FIGS. 2A-C.
Figure 3C:
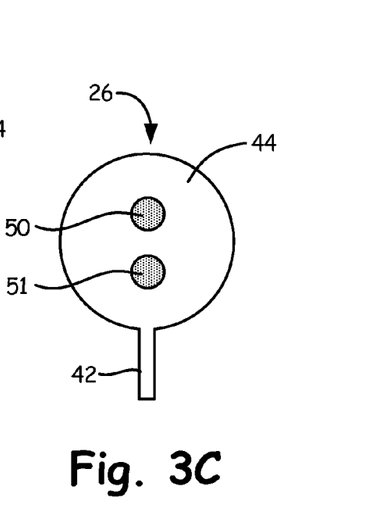

FIGS. 3A-C are schematic front views showing various exemplary configurations of the electrode structure 26. As shown in FIGS. 2A-C, respectively, the electrode structure 26 can be generally rectangular-shaped, oval-shaped or circular. In some embodiments, the backing 44 of the electrode structure 26 may have a flat, rectangular shape or an oval shape defined by a thickness T, width W, and an overall length L1 (see FIGS. 2A-C). In other embodiments, the electrode structure 26 may have a different form, for example, a circular shape, as shown in FIG. 3C, defined by a diameter and the thickness. It may be contemplated by those skilled in the art that the backing 44 may have various other forms suitable for neurostimulation implantation. In various embodiments, the material forming the electrode structure 26 may have a uniform or non-uniform cross-sectional thickness.

Figure 4:
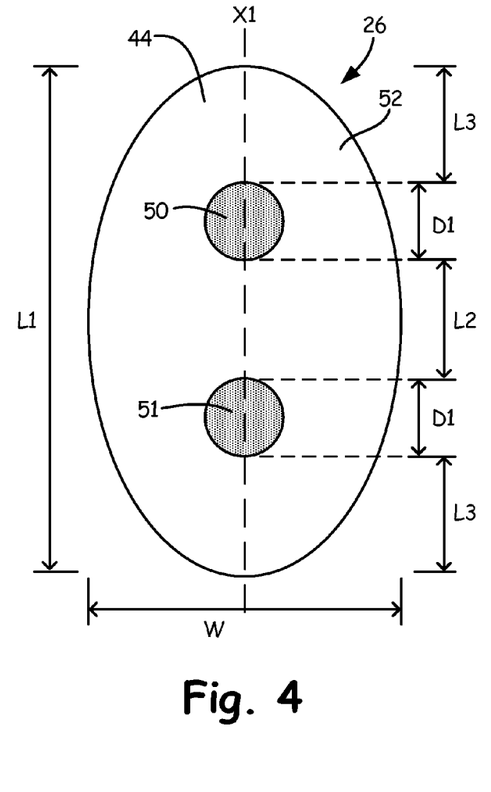
FIG. 4 is a front view of an electrode structure for the neurostimulation lead of FIGS. 2A-C, according to some embodiments.

FIG. 4 shows an exemplary electrode structure 26 having a flat, oval shape defined by a width W and an overall length L1. Suitable dimensions of the electrode structure 26 may allow a physician to more easily suture, or otherwise couple, the electrode structure 26 to the carotid sinus. In some embodiments, the dimensions of the electrode structure 26 may include an overall length (L1) range of about 13 mm to 18 mm, a width range of about 8 mm to 10 mm, and a thickness range of about 0.01 mm to 1 mm. For example, the electrode structure 26 may have a length L1 of 13 mm, a width W of 8 mm and a thickness T of 0.5 mm.

The overall length L1 and width W of the electrode structure 26 may affect the area available on the electrode structure 26 that may be used for placing a suture. For example, an electrode structure 26 having a length L1 of 13 mm and a width W of 8 mm would likely be sutured within about 3 mm or less from the outer perimeter of the electrode structure 26. In other examples, an electrode structure 26 having a length of 15 mm and a width of 10 mm would likely be sutured within about 4 mm or less from the outer perimeter of the electrode structure 26.

Figure 5:
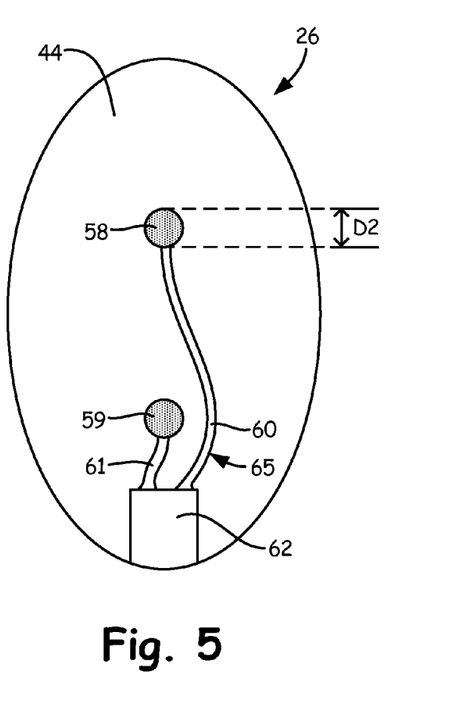
FIG. 5 is a front view of the electrode structure of FIG. 4 showing an interior of the electrode structure, according to some embodiments.

FIG. 5 is a schematic view of the electrode structure 26 showing an interior 65 of the backing 44 adapted to couple to a pair of electrodes 50, 51 to a pair of conductors (not shown). The interior 65 may also couple the pair of conductors to the distal end of the lead body 42 (not shown), in some embodiments. As shown, the interior 65 may include a pair of apertures 58, 59, a cavity 62, and a pair of channels 60, 61 connecting each aperture 58, 59 to the cavity 62.

As shown in FIGS. 4 and 5, the first surface 52 of the backing 44 may include the pair of apertures 58, 59 adapted to couple with the electrodes 50, 51, according to some embodiments. In some embodiments, the aperture 58 may be sized to partially or fully receive an electrode 50. For example, each aperture 58, 59 may have a diameter D2, or be otherwise sized, to receive at least a portion of the electrode 50, for example, a stem portion of an electrode 50.

The electrodes 50, 51 may be spaced a suitable distance apart from each other such that the sensing capability of each electrode 50 is unaffected by an adjacent electrode 51. In some embodiments, the edge-to-edge spacing L2 between the first electrode 50 to the second electrode 51 (see FIG. 4), e.g. the electrode-to-electrode spacing, may range from about 1 mm to 5 mm. For example, a suitable electrode-to-electrode spacing L2 may be 3 mm, in some embodiments.

The interior 65 of the backing 44 may also include multiple channels 60, 61 adapted to allow cables (not shown), and/or coils, to be disposed within the backing 44 and to couple to the electrodes 50, 51 according to some embodiments. In some embodiments, at least a portion of the interior 65, for example, the pair of channels 60, 61, may be enclosed between the first and second surfaces 52, 54 and the sides 56 (FIG. 2B) of the backing 44. In other embodiments, at least a portion of the interior 65 connects to one or more exterior surfaces of the backing 44, for example, the cavity 62 may connect to and form an opening at the sides 56 of the backing 44.

The channels 60, 61 may be spaced a suitable distance apart from each other such that the cables within the first and second channel 60, 61 do not interfere with one another and may be coupled to the appropriate electrodes 50, 51. In some embodiments, the first channel 60 may be spaced apart from the second channel 61 by a distance of at least 0.25 mm. For example, in some embodiments, the first channel 60 may be spaced apart from the second channel 61 by a distance ranging between about 0.5 mm and 1 mm.

The interior 65 of the backing 44 may also include the cavity 62 adapted to receive conductors and/or the distal end of the lead body 42, in various embodiments. The cavity 62 may be a generally tubular-shaped area adapted to receive conductors and/or at least a portion of tubing, such as a bi-lumen sheath, covering the lead conductors. As shown in FIG. 5, the cavity 62 allows a portion of the tubing covering the cables to be disposed within the backing 44.

In some embodiments, adhesive may be dispensed within the cavity 62 to bond the cables and sheath to the backing 44 of the electrode structure 26. Also, the cables and/or coils may be soldered, adhesively bonded, or joined by another commonly known bonding technique, to the electrodes 50, 51.

Figure 6:
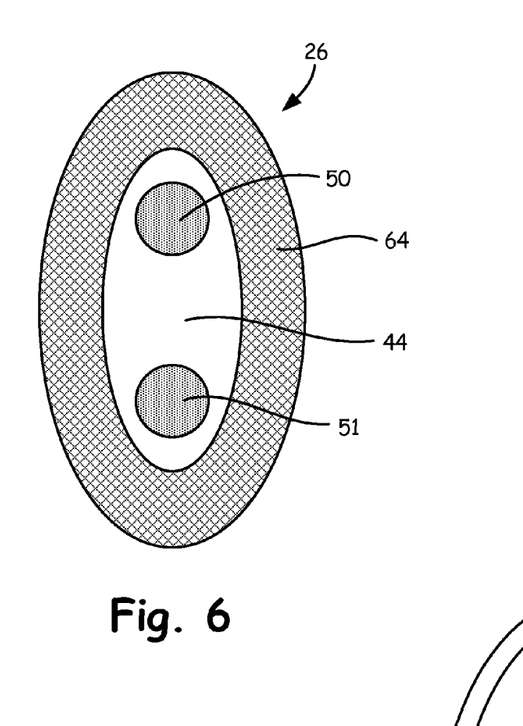
FIG. 6 is a front view of the electrode structure of FIG. 4 showing an embedded mesh within the electrode structure, according to some embodiments.

As shown in FIG. 6, at least a portion of the backing 44 may include a flexible material that includes an embedded mesh 64, in some embodiments. For example, the backing 44 may comprise a silicone material including an embedded mesh 64. In some embodiments, the mesh 64 may be disposed within a portion of the backing 44, such as the area proximate the outer perimeter, as shown in FIG. 6. In other embodiments, the mesh 64 may be disposed uniformly over the entire portion of the backing 44. Suitable materials for the embedded mesh 64 may include polyester or other commonly used materials in implantable products, in some embodiments. The mesh may minimize or aid in preventing the tearing of the backing when the backing is sutured onto an anatomical structure, such as a blood vessel.

In various embodiments, the embedded mesh 64 includes a fiber configuration that accommodates suturing while minimizing potential tearing of the backing 44. In some embodiments, the mesh 64 may comprise a plurality of randomly aligned fibers. In other embodiments, the mesh 64 may comprise fibers oriented in a repeating pattern or configuration. In some embodiments, the embedded mesh 64 may comprise tightly woven fibers. In other embodiments, the mesh 64 may comprise spaced-apart fibers such that a given fiber is spaced a suitable length from one or more neighboring fibers.

Figure 7:
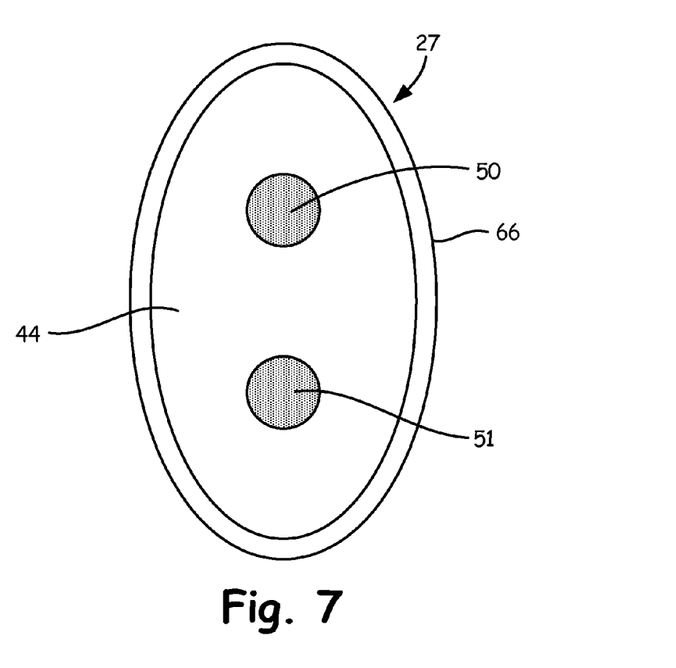
FIG. 7 is a front view of an alternative embodiment of an electrode structure, according to some embodiments.

In some embodiments, the outer perimeter of the backing 44 may be structurally adapted to minimize the propagation of tears should any form in the backing 44. As shown in FIG. 7, an alternative embodiment of the electrode structure 27 may be formed with the backing 44 having a raised outer rim 66, also described as a ridge or a lip structure. The outer rim 66 may increases the thickness of the backing 44 along the outer perimeter to minimize tearing during suturing, in some embodiments.

FIGS. 8-11 show various embodiments of grooves or through holes 68 of the backing 44 adapted to guide suture placement during device implantation. In some embodiments, the backing 44 of the electrode structure 26 may include one or more grooves 68, also described as indentations or depressions, extending along at least a portion of the first surface 52. The one or more grooves 68 are adapted to allow a suture to partially or fully seat within each groove 68, according to some embodiments.

Alternatively, in some embodiments, the backing 44 may include through holes 68 within the backing 44 that are adapted to receive a suture. For example, one or more through holes 68 may extend across at least a portion of the backing 44 from a first side 56 to a second opposite side 56 and within an area between the first surface 52 and the second surface 54.

Figure 8:
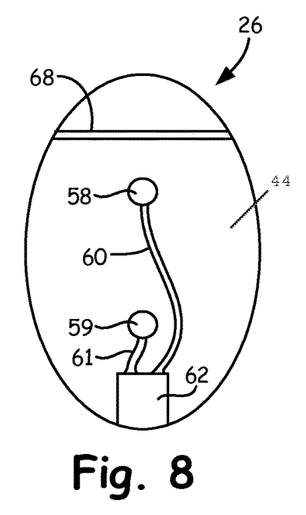
FIGS. 8-11 are schematic illustrations of various embodiments of an electrode structure showing features used for suture placement, according to some embodiments.
Figures 9, 10:
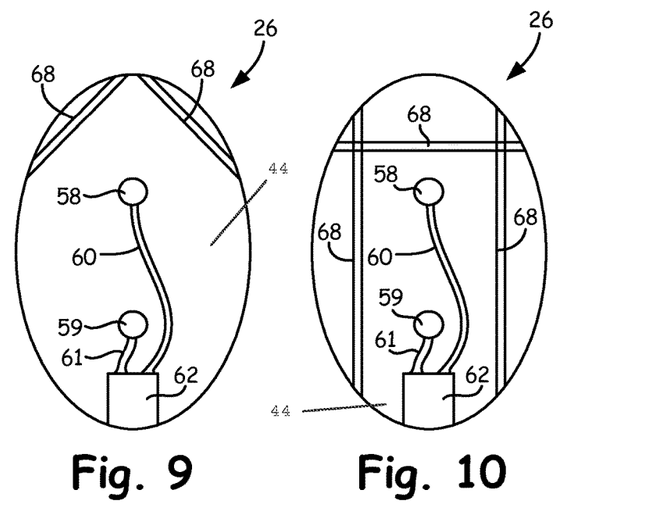
Figure 11:
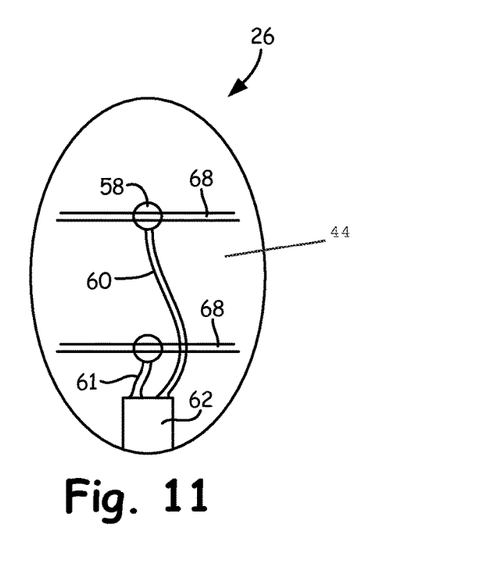

As shown in FIGS. 8-10, in some embodiments, the one or more grooves or through holes 68 may extend across at least a portion of the backing 44 adjacent to the interior cavities, e.g. the channels 60, 61 and the cavity 62. The grooves or through holes 68 may extend across portions of the backing as shown in FIG. 2A, e.g., the proximal portion 46, the distal portion 45, or both portions of the backing 44, according to some embodiments. Alternatively, as shown in FIG. 11, the grooves or through holes 68 may extend across portions of the backing 44 that overlap with the interior cavities, in certain embodiments. Such grooves or through holes 68 are adapted to extend in a plane superficial to the interior cavities, e.g. extend on a different plane, such that grooves or through holes 68 do not connect with the interior cavities of the backing 44. Adequate suture placement may allow electrodes 50, 51 (FIGS. 2A, 3A-C, 4, 6 and 7) to be placed closer to the vessel wall or an anatomical target, for example, the carotid sinus baroreceptors.

Figure 12:
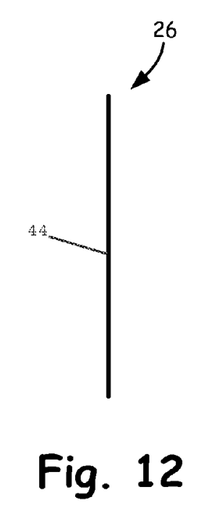
FIG. 12 is a top view of an electrode structure, according to some embodiments.
Figure 13:
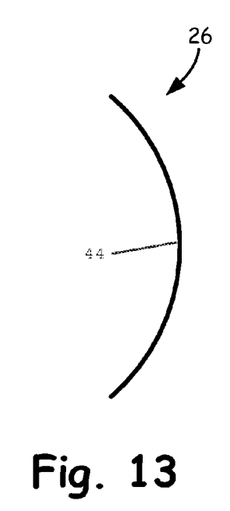
FIG. 13 is a top view of an electrode structure, according to some embodiments.

FIGS. 12 and 13 are top views of the electrode structure 26, according to some embodiments, showing the electrode structure in a straight configuration and a curved configuration, respectively. As shown by these figures, the backing 44 of the electrode structure 26 may be adapted to include a curved profile that complements the curved profile of a vessel wall. For example, the backing 44 may be formed into a C-shape, as shown in FIG. 13. In some embodiments, the curvature diameter of the backing 44 may range from about 5 mm to 15 mm. For example, when coupling the electrode structure 26 to the internal carotid having a diameter of approximately 10 mm, the curvature of the electrode structure 26 may range from about 8 mm to 12 mm.

The electrode structure 26 may serve as a coupling means for positioning two or more electrodes 50, 51 (FIGS. 2A, 3A-C, 4, 6 and 7) proximate to a blood vessel, for example, the carotid sinus. A carotid sinus stimulation system including a neurostimulation lead 18 coupled to the electrode structure 26 having two or more electrodes 50, 51 may provide improved identification of the area to be stimulated. The electrode structure 26 having at least two electrodes 50, 51 may allow for more than one vector for stimulation. The electrode structure 26 having at least two or more electrodes 50, 51 may also allow greater energy delivery by increasing the threshold for unwanted extraneous stimulation.

EXAMPLE 1

The present invention is more particularly described in the following example, which is intended as illustration only, since numerous modifications and variations within the scope of the present invention will be apparent to those skilled in the art.

Sample prototypes of an electrode structure were evaluated to determine a suitable length L1 based on a preclinical study using carotid sinus vessels of human models and cadavers.

Sample prototypes of the electrode structure for four test groups were constructed with varying overall lengths L1. Each test group had a sample size of three. The prototypes of this study were constructed using a 3D printer and were made of a standard 3D printing material.

The four test groups, including Groups A1 through A4, were constructed with varying body lengths L1. As shown in Table 1 below, the overall length of the samples of each test group was adjusted by varying the edge-to-edge distance between the first and second electrode L2 and the edge-to-edge distance between each electrode and the outer perimeter of the body L3 along a longitudinal axis X1 (see FIG. 4). The dimensions of all samples assumed a constant electrode diameter D1 of 2 mm.

TABLE 1

Sample Length Data

| Group | Overall Length L1 (mm) | L2 (mm) | L3 (mm) |
|---|---|---|---|
| A1 | 12 | 2 | 3 |
| A2 | 16 | 2 | 5 |
| A3 | 13 | 3 | 3 |
| A4 | 17 | 3 | 5 |

Figure 14:
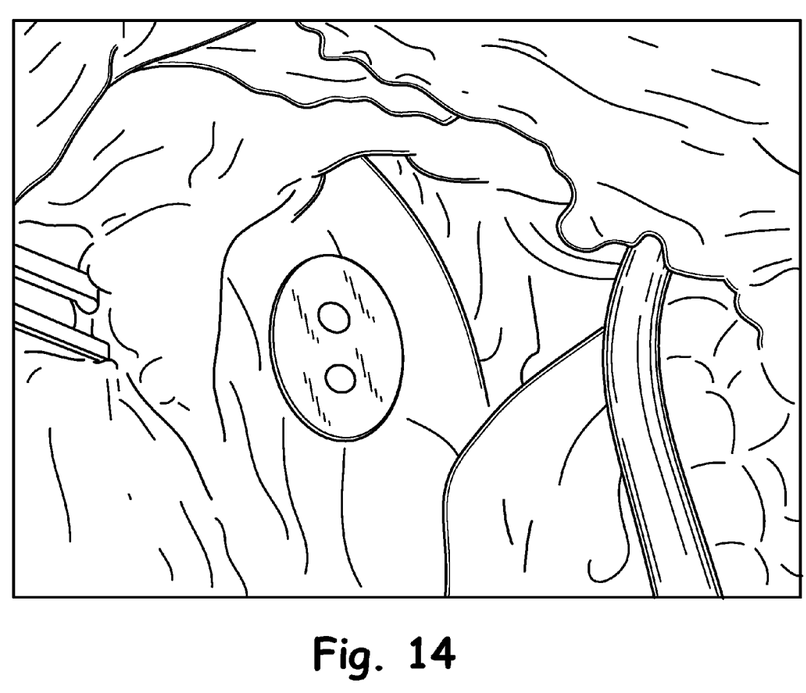
FIG. 14 is an image of an electrode structure sutured to a blood vessel.

Each sample was sutured to a carotid sinus of a human cadaver by a veterinarian (see FIG. 14) and subjectively assessed by engineers. Groups A1 and A3 were assessed as having a suitable length L1 that would be likely compatible for suturing to the carotid sinus in humans. In contrast, Groups A2 and A4 were assessed as likely having too large a length L1 and likely being incompatible for carotid sinus suturing. The results of this study suggest that a suitable length for the electrode structure ranges from about 12 mm to 13 mm.

EXAMPLE 2

The present invention is more particularly described in the following example, which is intended as illustration only, since numerous modifications and variations within the scope of the present invention will be apparent to those skilled in the art.

Sample prototypes of electrode structure bodies were evaluated to determine suitable dimensions based on a preclinical study using carotid sinus vessels of human models and cadavers.

The samples for three test groups, including Groups B1 through B3, were constructed using a silicone material. A sample size of three was used for each test group.

Figure 15:
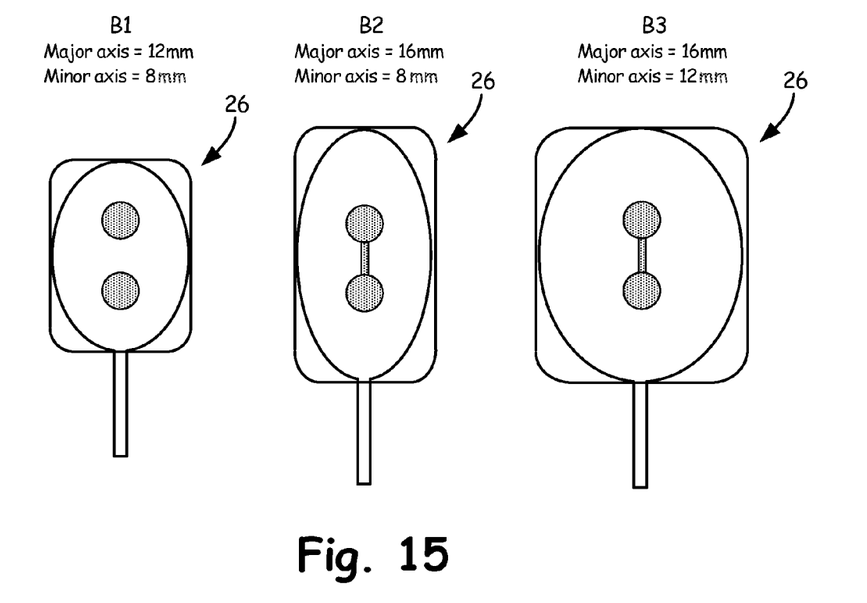
FIG. 15 provides schematic illustrations of various samples of an experiment.

As shown in Table 2 and FIG. 15, the test groups B1-B3 were constructed with varying body lengths L1 and widths W. The overall length of samples in each test group was adjusted by varying the edge-to-edge distance between the first and second electrode L2 and the edge-to-edge distance between each electrode and the outer perimeter of the body L3 along a longitudinal axis X1 (see FIG. 4). The samples of all test groups assumed a constant electrode diameter D1 of 2 mm.

TABLE 2

| Group | Sample Dimension Data | | | |
| --- | --- | --- | --- | --- |
| | Overall Length L1 (mm) | L2 (mm) | L3 (mm) | Width W (mm) |
| B1 | 12 | 2 | 3 | 8 |
| B2 | 16 | 2 | 5 | 8 |
| B3 | 16 | 3 | 3 | 12 |

Each sample was sutured to a carotid sinus of a cadaver by a surgeon and subjectively assessed by surgeons and engineers. Group B1 was assessed as being likely suitable for vessel suturing to the carotid sinus of a human. Groups B2 and B3, however, were assessed as likely being too large and therefore likely unsuitable for carotid sinus suturing. Based on these results, the electrode structure body having a length of about 12 mm and a width of about 8 mm would likely be a suitable dimension for an electrode structure body targeting the human carotid sinus.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electrode structure for an implantable stimulation lead for use in stimulating a target nerve structure within a patient, the electrode structure comprising:
a flexible backing defined by a major dimension extending in a direction of a first axis, and a minor dimension extending generally orthogonal to the first axis, the backing including a first surface, a second surface opposite the first surface, and a plurality of sides extending between the first surface and the second surface;
a plurality of electrodes coupled to the backing and disposed on the first surface; and
at least one through hole extending across the backing, the through hole extending from one of the plurality of sides to another one of the plurality of sides and within an area between the first surface and the second surface.

2. The electrode structure of claim 1, wherein the backing is adapted to be coupled to a distal end of an implantable lead in situ.

3. The electrode structure of claim 1, wherein the backing is configured to resist suture tearing.

4. The electrode structure of claim 1, wherein at least a portion of the backing element includes an embedded mesh.

5. The electrode structure of claim 1, wherein the backing has a curved shape adapted to conform to a curvature of a blood vessel.

6. A neurostimulation lead comprising:
a lead body having a proximal portion and a distal portion;
a first conductor extending through the lead body; and
an electrode structure secured to the distal portion of the lead body, the electrode structure including:
a backing defined by a major dimension generally in a direction of a longitudinal axis defined by the distal portion of the lead body and a minor dimension generally in a same plane and orthogonal to the longitudinal axis, the backing including a first surface, a second surface opposite the first surface, and a plurality of sides extending between the first surface and the second surface;
a plurality of electrodes coupled to at least a portion of the backing and disposed on the first surface; and
at least one through hole extending across the backing, the through hole extending from one of the plurality of sides to another one of the plurality of sides and within an area between the first surface and the second surface.

7. The neurostimulation lead of claim 6, wherein the backing is generally rectangular in shape.

8. The neurostimulation lead of claim 6, wherein the backing has peripheral edges that are generally rounded.

9. The neurostimulation lead of claim 6, wherein the backing is generally oval shaped.

10. The neurostimulation lead of claim 6, wherein the backing is curved about a central axis generally parallel to a longitudinal axis.

11. A neurostimulation system comprising:
a pulse generator comprising a power source; and
a lead comprising:
a lead body having a proximal portion and a distal portion, the proximal portion of the lead secured to the pulse generator;
a first conductor extending through the lead body; and
an electrode structure secured to the distal portion of the lead body, the electrode structure including:
a backing defined by a major dimension generally in a direction of a longitudinal axis defined by the distal portion of the lead and a minor dimension generally in a same plane and orthogonal to the longitudinal axis, the backing including a first surface, a second surface opposite the first surface, and a plurality of sides extending between the first surface and the second surface;
a plurality of electrodes coupled to at least a portion of the backing and disposed on the first surface; and
at least one through hole extending across the backing, the through hole extending from one of the plurality of sides to another one of the plurality of sides and within an area between the first surface and the second surface.

12. The neurostimulation system of claim 11, wherein the backing includes a flexible material that includes a mesh.

13. The neurostimulation system of claim 12, wherein the mesh is disposed in an area proximate to an outer perimeter.

14. The neurostimulation system of claim 12, wherein the mesh is disposed uniformly over an entire portion of the backing.

15. The neurostimulation system of claim 12, wherein the mesh comprises polyester.

16. The neurostimulation system of claim 11, wherein the at least one through hole extends across one of a proximal portion of the backing, a distal portion of the backing or a combination thereof.

17. The neurostimulation system of claim 11, wherein the major dimension of the backing ranges from about 12 mm to about 16 mm.

* * * * *